US008722644B2

(12) United States Patent
Wu

(10) Patent No.: US 8,722,644 B2
(45) Date of Patent: May 13, 2014

(54) MIXTURE OF HYALURONIC ACID FOR TREATING AND PREVENTING PEPTIC ULCER AND DUODENAL ULCER

(75) Inventor: Tsung-Chung Wu, Taipei County (TW)

(73) Assignee: Holy Stone Healthcare Co., Ltd., Taipei (TW)

( * ) Notice: Subject to any disclaimer, the term of this patent is extended or adjusted under 35 U.S.C. 154(b) by 72 days.

(21) Appl. No.: 13/407,637

(22) Filed: Feb. 28, 2012

(65) Prior Publication Data

US 2012/0157408 A1 Jun. 21, 2012

Related U.S. Application Data

(63) Continuation-in-part of application No. 12/651,806, filed on Jan. 4, 2010, now abandoned.

(51) Int. Cl.
*A01N 43/04* (2006.01)
*A61K 31/715* (2006.01)

(52) U.S. Cl.
USPC .......................................................... 514/54

(58) Field of Classification Search
None
See application file for complete search history.

(56) References Cited

U.S. PATENT DOCUMENTS

| 5,888,986 A | 3/1999 | Morales et al. |
|---|---|---|
| 6,656,921 B1 | 12/2003 | Illes et al. |
| 7,834,173 B2 | 11/2010 | Pietrangelo et al. |
| 8,034,795 B2 | 10/2011 | De Luca et al. |
| 2005/0080037 A1 | 4/2005 | Petrella |

FOREIGN PATENT DOCUMENTS

| BE | 904547 | 10/1986 |
|---|---|---|
| HU | 203372 | 7/1991 |
| TW | 087106525 | 4/1998 |
| WO | WO87/05517 | 9/1987 |

OTHER PUBLICATIONS

Chung et al. JP 2011037853 A, published Feb. 24, 2011, machine translation and abstract.*
Wu, JP 2011037849 A, published Feb. 24, 2011, machine translation and abstract.*
Gomis et al., *Arthritis & Rheumatism*, vol. 50, No. 1, Jan. 2004, pp. 314-326.

* cited by examiner

*Primary Examiner* — Layla Bland
(74) *Attorney, Agent, or Firm* — Muncy, Geissler, Olds & Lowe, P.C.

(57) ABSTRACT

The present invention is related to a method of treating and preventing peptic ulcer and duodenal ulcer by administering hyaluronic acid composition with a binary mixture of hyaluronic acids having mainly different weight-average molecular weight and then different rheological, scaffold and degradation properties in aqueous solution. The resulted compositions have demonstrated an optimal balance between adhesion, tissue scaffold and treating time to the peptic and duodenal ulcer and bleeding. Thus, the present inventive binary mixture exhibits a quick and lasting effect on the treatment and prevention of duodenal or peptic ulcer and bleeding.

6 Claims, 6 Drawing Sheets

MIXTURE OF HYALURONIC ACID FOR TREATING AND PREVENTING PEPTIC ULCER AND DUODENAL ULCER

CROSS-REFERENCE TO RELATED APPLICATIONS

This application is a Continuation-in-part of U.S. patent application Ser. No. 12/651,806 filed on Jan. 4, 2010 now abandoned, that is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

BACKGROUND OF THE INVENTION

1. Field of the Invention

The present invention provides a method for treating and preventing a subject suffering from peptic ulcer and duodenal ulcer.

2. Description of the Related Art

As generally known a peptic ulcer, also known as PU or peptic ulcer disease, is an ulcer (defined as mucosal erosions equal to or greater than 0.5 cm) of an area of the gastrointestinal tract that is usually acidic and thus extremely painful. Almost 70-90% of ulcers are associated with *Helicobacter pylori*, a spiral-shaped bacterium that lives in the acidic environment of the stomach. Ulcers can also be caused or worsened by drugs such as aspirin, Plavix (clopidogrel), ibuprofen, and other NSAIDs (non-steroid anti-inflammatory drugs).

Contrary to general belief, more peptic ulcers arise in the duodenum (first part of the small intestine, just after the stomach) rather than in the stomach. Duodenal ulcers are generally benign.

The classification of peptic ulcer by region or location includes:
Stomach (called gastric ulcer)
Duodenum (called duodenal ulcer)
Esophagus (called Esophageal ulcer)
Meckel's Diverticulum (called Meckel's Diverticulum ulcer)

Furthermore, modified Johnson classifications of peptic ulcer include:
Type I: Ulcer along the body of the stomach, most often along the lesser curve at incisura angularis along the locus minoris resistentiae.
Type II: Ulcer in the body in combination with duodenal ulcers. Associated with acid oversecretion.
Type III: In the pyloric channel within 3 cm of pylorus. Associated with acid oversecretion.
Type IV: Proximal gastroesophageal ulcer.
Type V: Can occur throughout the stomach. Associated with chronic NSAID and ASA use.

Hyaluronic acid, also known as hyaluronan, hyaluronate or sodium hyaluronate, is generally referred to as HA, which is a natural glycosaminoglycan macromolecule including disaccharides composed of the alternative N-acetyl-D-glucosamine and D-glucuronic acid linked via alternative β-1,3 and β-1,4 glycosidic bonds. HA found in nature with a molecular weight (Mw) between 50,000 Dalton (Da) and a few million Dalton usually has high viscosity.

The species of HA is not only being shown as Mw but also as intrinsic viscosity ($\eta$) which is directly related to the Mw of a polymer through the Mark-Houwink-Sakurada (MHS) equation: $[\eta]=KM^{\alpha}$. For HA, K is 0.397 and the exponent $\alpha$ is 0.601 dissolving in 0.15 N NaCl at a concentration ranging between 0.01 mg/ml and 0.1 mg/ml (Gomis et al., Arthritis & Rheumatism Vol. 50, No. 1, January 2004, p 316).

The HA can be found in the soft connective tissue in the body of mammals, and the skin, the vitreous humor of the eye, the joint fluid, the umbilical cord and cartilage tissue contains higher volume of the HA. The HA can be applied as the adjuvant agent for the eye operation, or to reduce the pain while movement of the knee and joint of the osteoarthritis patients.

U.S. Pat. No. 5,888,986 discloses a method and related structure for using HA at an effective concentration to treat cystitis, wherein the average Mw of the HA is more than 200,000 Da. There is only one species of HA with a certain Mw been applied in the embodiment thereof. For example, HA with the average molecular weight of 650 KDa or 1,900 KDa is used to treat the cystitis; however, the single species of HA with the certain average molecular weight cannot be used for both prompt treatment and sustained effect.

Richter Gedeon Vegyeszeti Gyar R. T., a Hungarian company, has filed a U.S. Pat. No. 6,656,921 (Pat. '921) on Dec. 2, 2003 in title of Use of zinc hyaluronate against peptic ulcer to disclose that the zinc hyaluronate with Mw between 500 KDa and 1,200 KDa can be applied to treat peptic ulcer.

The preparation of 1.0% Solution of Zinc Hyaluronate of the Pat. '921 is as follows:

Sodium hyaluronate (1.0 g) is swollen in 30 ml of water while constant stirring then after adding 18.75 ml of 0.1 molar zinc chloride solution it is filled to 100 ml with distilled water. The characteristics of sodium hyaluronate used for the preparation of solutions of zinc hyaluronate with various molecular weights and degrees of purity employed in our pharmacological investigations are summarized in the following Table (Pat. '921, page 4, line-31).

Zinc is a heavy metal which may have different effects or side effects on various individuals, or may raise the burden of body health, though it belongs to trace element required by human body. The purpose of Pat. '921 to use zinc is to promote the treatment effect for peptic ulcer. However, the dosage and treatment duration in the clinical must be strictly restricted owing to zinc involved. Furthermore, Pat. '921 only used one species of HA and did not depict or give any embodiment to teach at least two species HA exploited at the same time.

Gomis et al. (Arthritis & Rheumatism Vol. 50, No. 1, January 2004, pp. 314-326) disclosed a comparison among 3 different HAs preparations used as therapeutic agents for osteoarthritis pain in humans in order to establish the degree to which a single application affects the sensitivity of nociceptors in both the normal and the acutely inflamed rat joint. Three HAs were all commercially available. The average Mw of Orthovisc, calculated from intrinsic viscosity and light scattering measurements, is higher than that of Hyalgan (1.3 million versus 0.7 million), whereas Synvisc is about 6 million (Gomis et al., p 316, Table 1). According to the certificate of analysis (COA) of different commercial products, the average Mw has been decided in different polydispersity. The polydispersity revealed in Gomis et al. cannot represent the whole situation in the market.

HA can be defined either by average molecular weight or by intrinsic viscosity which is well known in this technology field (Gomis et al., p 316, Table 1). The specific molecular weight of HA cannot be defined precisely, but could be defined as the content of certain HA is especially high in particular molecular weight (Gomis et al. p 316, FIG. 1). Moreover, molecular weight of HA can be defined by HPLC which is also well known in the art. Some examples are shown as follows:

(a) The molecular weight of hyaluronic acid may be determined according to a conventional manner, for example by gel permeation chromatography (GPC) (U.S. Pat. No. 7,834, 173, Page 4, line 49).

(b) High pressure liquid chromatography (HPLC)-GPC analysis reveals that the fraction of HA obtained has a mean molecular weight (Mw) of 5,850, a mean numerical molecular weight (MN) of 3,640 and a polydispersity index of 1.61 (U.S. Pat. No. 8,034,795, example 4, page 22, line 17).

Therefore, the term "average molecular weight" as a definition to distinguish HA is generally acknowledged by skilled artisan in the art.

SUMMARY OF THE INVENTION

The present invention provides a method for treating and preventing a subject suffering from peptic ulcer and duodenal ulcer, comprising a step of administering to the subject a therapeutically effective amount of a hyaluronic acid mixture including a low average molecular weight hyaluronic acid (LMWHA) and a high average molecule weight hyaluronic acid (HMWHA), wherein the average molecular weight (Mw) of LMWHA is lower than 1.5 million Da, and the average Mw of HMWHA is higher than 1.5 million Da, wherein the average Mw of LMWHA is apart from the average Mw of HMWHA by at least 0.5 million Da, and a mixing ratio of the LMWHA and the HMWHA is in a range from 20:80 to 80:20 by weight.

DETAILED DESCRIPTION OF THE INVENTION

Figure 1:
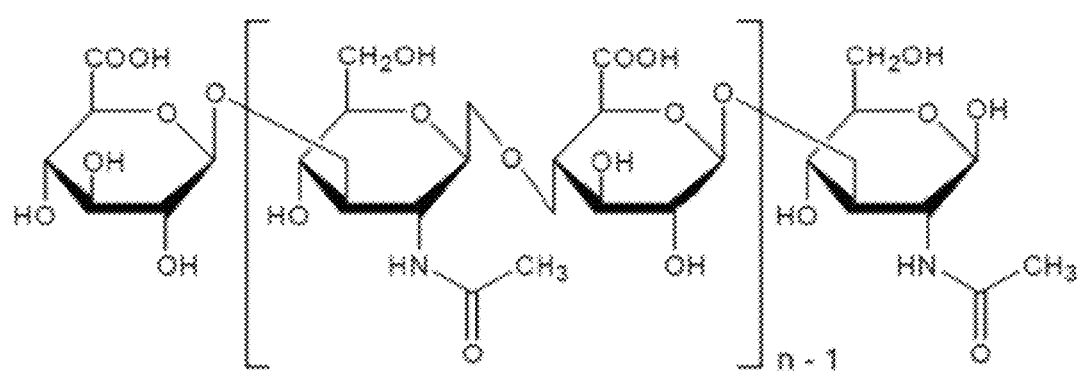
FIG. 1 shows the general chemical structure of hyaluronic acid.

The hyaluronic acid (HA) mixture of the present invention used to treat and prevent the peptic ulcer and the duodenal ulcer comprises at least two average molecular weight of HAs with mixed the low average molecule weight hyaluronic acid (LMWHA) and the high average molecule weight hyaluronic acid (HMWHA). The different Mw has different rheology, functions of tissue scaffold and degradation in the solution; therefore, the HA mixture can balance the effect and the degradation of HA in order to treat and to prevent peptic ulcer and the duodenal ulcer and bleeding, as well as to have a prompt and rapid effect and a longer treatment effect. The general chemical structure of the hyaluronic acid is illustrated as FIG. 1.

DEFINITION OF THE PRESENT INVENTION

LMWHA (low average molecular weight hyaluronic acid): the average Mw is lower than 1.5 million Da, and the range of preferred LMWHA is within 0.5 million to 1.5 million Da.

HMWHA (high average molecular weight hyaluronic acid): the average Mw is higher than 1.5 million Da, and the range of preferred HMWHA is within 1.5 million to 3.5 million Da.

The definition of HMWHA and LMWHA is differentiated by 1.5 million Da hereupon is pertaining to the experience of the inventor himself, the technical content of the present invention and the characteristic of the technology field. This is the relatively well criteria to fit the present invention. In view of the criteria, the speciality of the present invention is performed best when mixing HMWHA and LMWHA of the present invention. The speciality of the present invention is that the LMWHA can adhere to intestinal mucosa quickly whereas the HMWHA can be degraded naturally to compensate the LMWHA though the adherence effect is lower for HMWHA. The result of the present invention so as to extend treatment process by supplying the mixture of the present invention merely once which is superior to only treat by single HA. Moreover, the threshold of 1.5 million Da of the present invention did not be taught by any prior art.

The formulation with the LMWHA and the HMWHA can promptly cover and adhere to the inflammatory portion by LMWHA to treat the peptic ulcer and the duodenal ulcer, and to sustain the process by the degradation of HMWHA to LMWHA for extending the effect, thus to achieve prompt treatment and sustained effect.

Using biomaterial with no side effect is one of the biggest characteristics of the present invention. The ingenuity of the present invention to mix HMWHA and LMWHA is used to extend and simplify treatment effect depending on its natural characteristic of HA only, and this ingenuity did not be taught by prior art. Even the reference Gomis et al. also did not teach the way of mixing HMWHA and LMWHA to treat disease other than joint problem or enhance the merit of the mixture. Furthermore, no animal teat result of treating PU and DU is shown in Gomis et al.

The characteristics of physical, chemical, biological and the effect or function of HA are different when the average molecular weight of HA is variant. This opinion can also be verified by experimental data in FIGS. 4 to 6 in the Gomis et al. Therefore, the innovative concept of mixing high and low average molecular weight of HAs of the present invention as a technical difference refer to the prior art has theoretical basis.

Comparing with U.S. Pat. No. 6,656,921 (Pat. '921), the present invention especially emphasizes the characteristics, functions and highlights of the mixture of HMWHA and LMWHA which is absent in the Pat. '921. The other major contribution of the present invention comparing with the Pat. '921 or other prior art is providing a simple, convenient and no side effect therapy to treat disease inside the animal body because HA is naturally exist inside the animal body.

Figure 2:
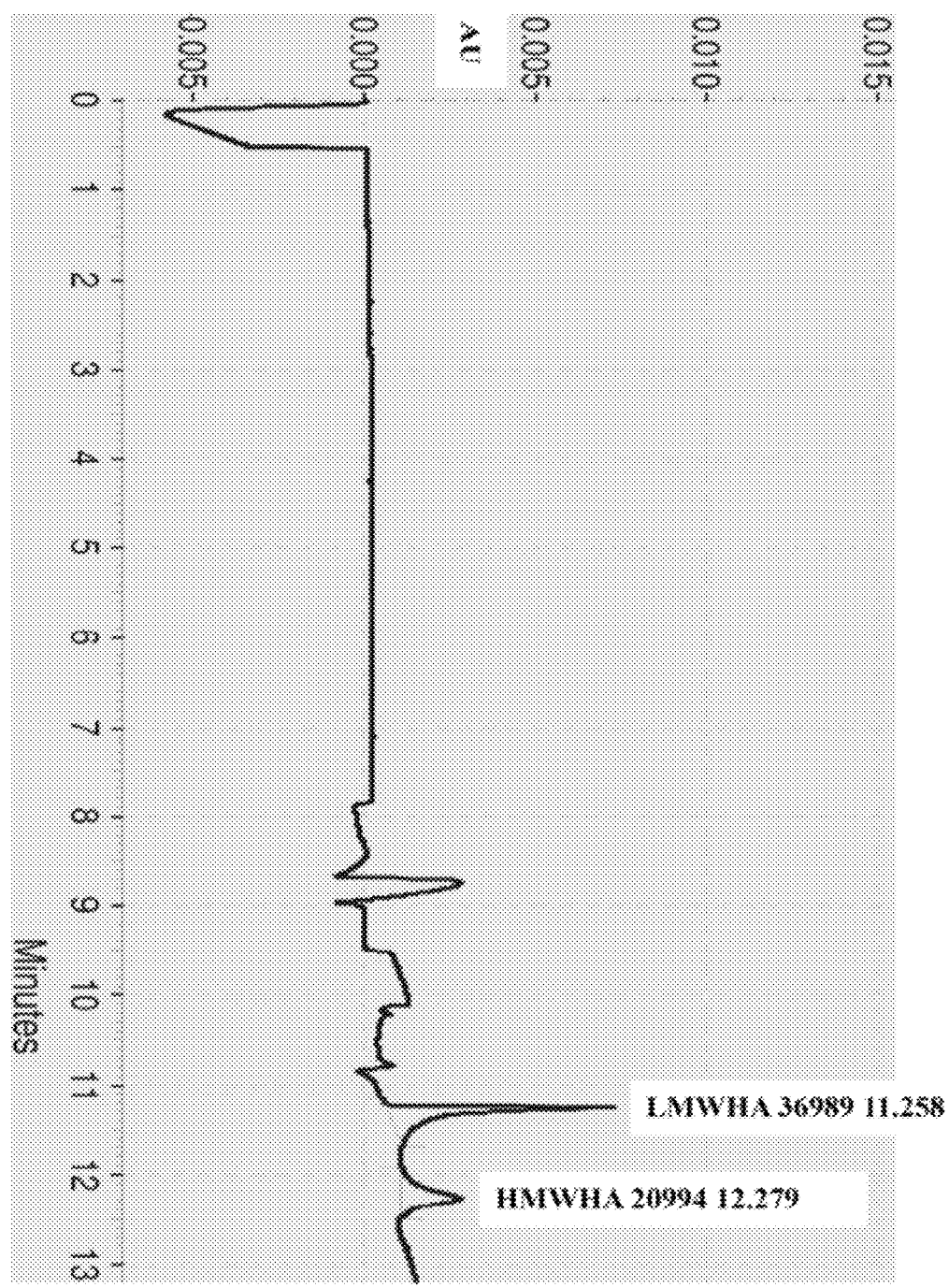
FIG. 2 shows the extractions of LMWHA and HMWHA independently after the capillary electrophoresis analysis. Y axis means AU (Absorbance Unit, UV 200 nm); X axis means minutes. The data above the peak means name of sample, area (calculated by integrate) and time from down to top.

The LMWHA and the HMWHA of the present invention can be differentiated sharply by CE (capillary electrophoretic) even both HAs were mixed in the same solution (FIG. 2). This example is represented by 350 KDa (LMWHA) and 2000 KDa (HMWHA) which are both commercial available from Shandong Freda Medical Device Co., Ltd. (Freda). The result explains no interconnective reaction happened between LMWHA and HMWHA, or they should not be recognized so sharply. Comparing with Gomis et al., both results all indicate that average molecular weight hyaluronic acid may determined by different commercial products made by different companies. Therefore, the definition of the LMWHA and the HMWHA of the present invention is proper for practical use.

Figure 3:
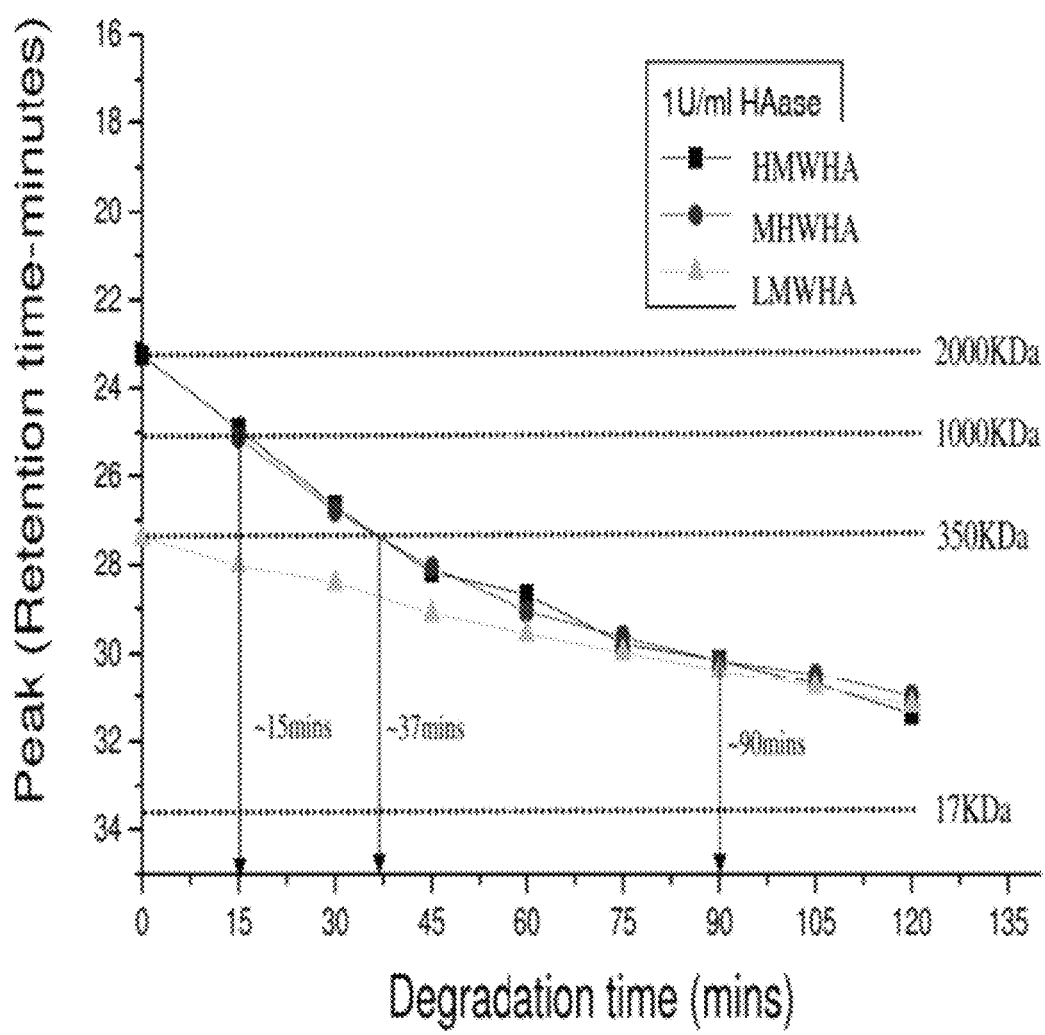
FIG. 3 shows the retention time of HAs by GPC diagram, wherein the vertical axis represents the retention time in GPC, and the horizontal axis represents the degradation time of HA in a solution containing HAase.
Figure 4:
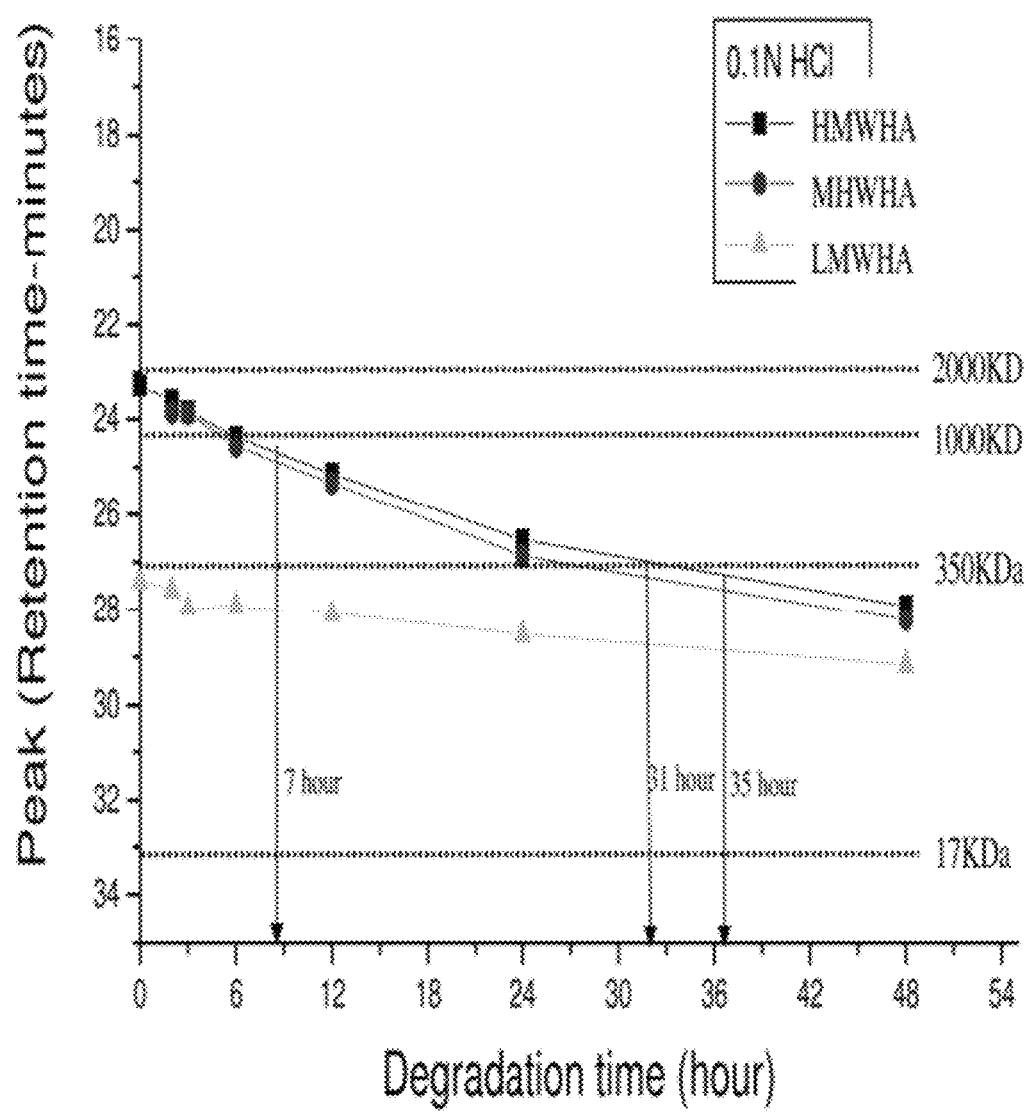
FIG. 4 shows the retention time of HAs by GPC diagram, wherein the vertical axis represents the retention time in GPC, and the horizontal axis represents the degradation time of HA in artificial gastric juice.

The present invention provides results that HMWHA can compensate LMWHA even under action of HAase (FIG. 3) or artificial gastric juice (FIG. 4). The results indicate that HA can be replenished in the situation of HAase exist or in the gastrointestinal environment to keep a long term effect. The retention time was obviously increased followed by the increased incubation of all three HAs under HAase (FIG. 3). The retention time was slowly increased followed by the increased incubation of all three HAs under acidic environment (FIG. 4). The simulated physiological situations were used to proceed in experimental parameters, but true physiological environments are more complicated that may cause slightly different result. However, the trend of HA incubation will not be changed owing to its nature molecular characteristic which HMWHA can compensate LMWHA.

Figure 5:
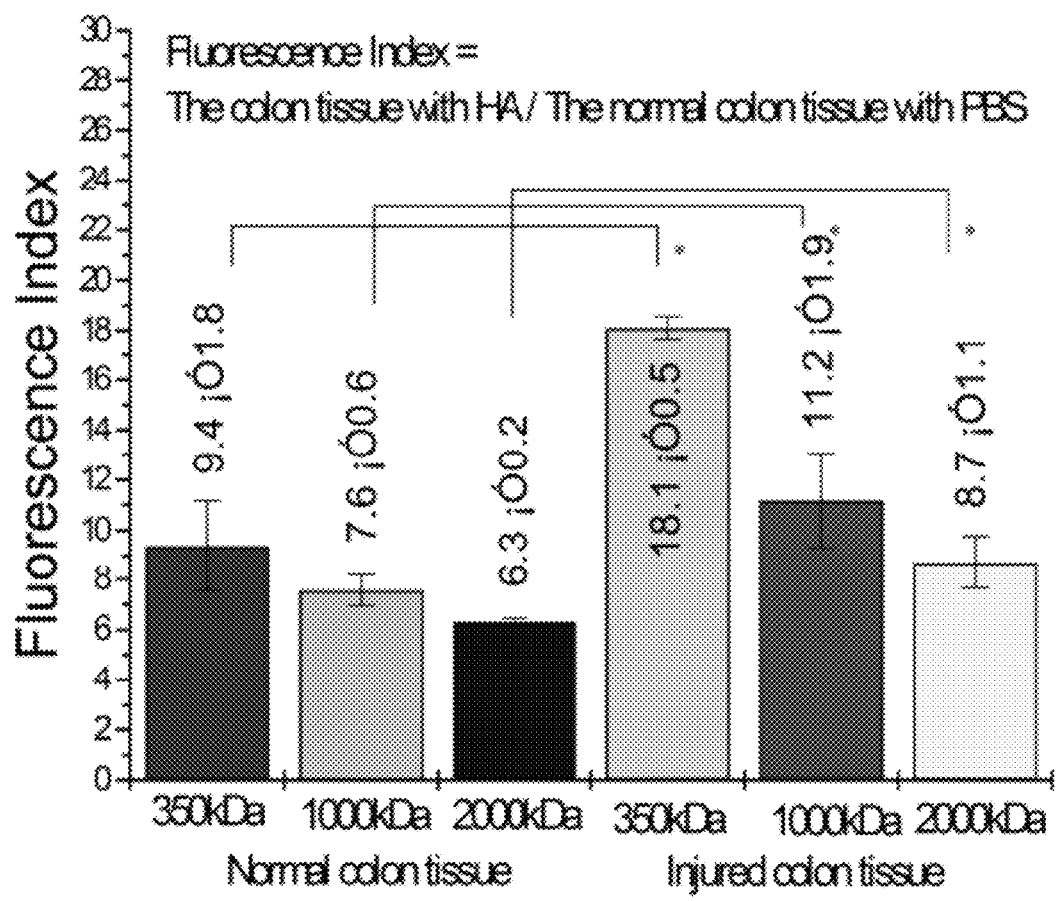
FIG. 5 shows the affinity of HAs by fluorescent index in normal and injured colon tissues.

The result of the present invention shows that the HAs with the same average Mw were adhered to the injured colon tissues obviously higher than in the normal colon tissues (P<0.01, FIG. 5). Comparing the differences among HAs of three average molecular weights which were adhered to the injured colon tissues, the fluorescent index of adhesion of 350 KDa HA by the injured colon tissues was obviously higher than the HAs of the other two average molecular weights (2000 KDa and 1000 KDa). Further, the fluorescent index of adhesion of 1000 KDa HA by even normal or injured colon tissues was higher than 2000 KDa HA. This result explains fast dispersed and covered effect of low Mw HA which supplies instant wound healing and protection of the gastrointestinal tissue from being injured further.

The present invention provides a preferred embodiment to explain the effect and function of HA mixture (hereby code: PU98) of the present invention. The evidences approved that the subject matter in the present invention has even animal test to verify while comparing with the references abovementioned that have not had animal test result to depict the effect of HA mixture defined in the present invention.

Figure 6:
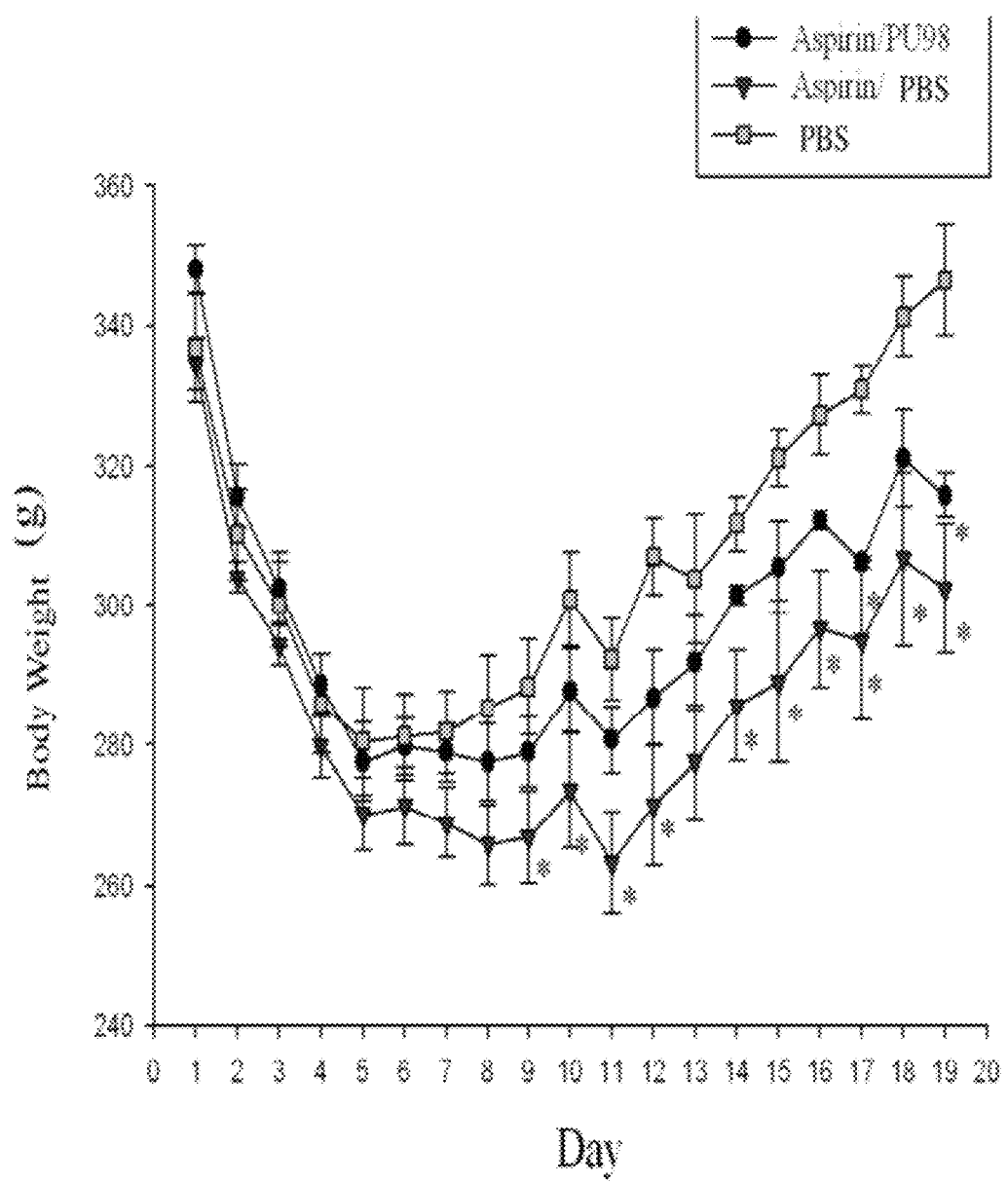
FIG. 6 shows changes in weight of rats during test period. All rats were divided into three groups: study group (Aspirin/PU98), placebo group (Aspirin/PBS), control group (PBS). From the 9th day weight loss was observable in the placebo group where it fell below control group (*$P<0.05$).

The present invention used the changes of average body weight as an index to evaluate the amelioration of PU. After dissection of the rats from each group, study group (Aspirin/PU98), placebo group (Aspirin/PBS) and control group (PBS), in terms of weight, the placebo group during D9-D19 (Day) showed significant weight loss when compared to the control group (FIG. 6). While comparing control group with placebo group, this result provides that the induction model utilized in the present invention obviously and effectively causes gastric inflammation in animals, affecting digestion and absorption. During the period of inflammation, rats given no treatment (placebo group) showed least average body weights recovery than either the control group or the study group; however, when given PU98 (mixture of HMWHA and LMWHA), the trend of study group shown that PU98 has better effect to ameliorate ulcer than placebo group induced by aspirin on the weight. Therefore, the therapy effect of PU98 can be confirmed even that aspirin was administered everyday in study group while comparing with placebo group. In terms of weight, PU98 shows the potential to reduce gastrointestinal inflammation by rats model induced by aspirin.

A preferred embodiment of the present is to provide a method for treating and preventing a subject suffering from peptic ulcer and duodenal ulcer, comprising a step of administering to the subject a therapeutically effective amount of a HA mixture including a low average molecular weight hyaluronic acid (LMWHA) and a high average molecule weight hyaluronic acid (HMWHA), wherein the average molecular weight (Mw) of LMWHA is lower than 1.5 million Da, and the average Mw of HMWHA is higher than 1.5 million Da.

Another preferred embodiment of the present invention is to provide a 1:1 mixture of the LMWHA and the HMWHA in the salt form of the HA, and adjust the mixture ratio between 20:80 and 80:20 depending on the clinical purpose. The HA mixture with a higher ratio of LMWHA can be more rapidly in the treatment. To the contrary, with a higher ratio of HMWHA can have a better prolonged degradation effect. The dilution solution hereby used is preferred phosphate buffered saline (PBS) or pharmaceutical buffer solution in a concentration range of 0.5 mg/ml to 10 mg/ml with HA mixture hereof.

Another preferred embodiment of the present invention is to provide a method of treating PU and DU including a HA mixture of both LMWHA and HMWHA that can be a major ingredient with the proper excipient to formulated as oral solid dosage form, the oral solution or suspension or injection solution; and wherein administration routes includes oral or endoscope injection.

Another preferred embodiment of the present invention is to provide a HA mixture including LMWHA and HMWHA that can be further conjunctively used with a coagulant, antacid, H2 blocker, the potassium hydrogen ion pump blocker or the peptic mucosa protector as the adjuvant to potentiate the therapeutic or drug effect.

Another preferred embodiment of the HA mixture of the present invention is also treating and preventing bleeding caused by peptic ulcer or duodenal ulcer.

According to the present invention, the oral formulation (for example capsule), the above HA mixture is the active ingredient mixed with excipient (for example starch or carboxy methyl cellulose (CMC)) to form the capsule, the HA mixture will dissolve and disperse in the stomach and form a protective membrane at the peptic ulcer region in order to accelerate healing of the inflammatory region and also to achieve sustained effect.

For oral formulation (for example oral solution), the above HA mixture is the active ingredient mixed with the excipient (for example phosphate buffered saline (PBS solution) or suspension formulation) to form the oral solution, the invented mixture will spread quickly in the stomach and form a protective membrane at the peptic ulcer region in order to accelerate healing of the inflammatory region and also to achieve sustained effect.

For endoscope injection formulation (for example injection solution), the above HA mixture is the active ingredient mixed with the excipient (for example phosphate buffered saline (PBS solution) or suspension formulation) to form the injection solution, the hyaluronic acid mixture can be injected through the endoscope directly into the inflammatory portion to form a protective membrane at the peptic ulcer region in order to accelerate the healing of the inflammatory region and also to achieve sustained effect to shorten the treatment.

The preferred concentration of the hyaluronic acid mixture ratio of the LMWHA and the HMWHA or the pharmaceutically acceptable salt thereof is in a range from 0.5 mg/ml to 10 mg/ml, but the preferred concentration in liquid formulation is in a range from 0.05% to 1% (w/v).

According to the above description, at least two or more than two pharmaceutically acceptable salt of the hyaluronic acid may be used to form a hyaluronic acid mixture with different Mw to rapidly forms a coating at the inflammatory surface and prolonged effect by the prolongation of the degradation, and thus achieve a faster treatment and sustained effect to shorten the treatment time.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations in which fall within the spirit and scope of the included claims. All matters set forth herein or shown in the accompanying drawings are to be interpreted in an illustrative and non-limiting sense.

EXAMPLE

Example 1

Determination of LMWHA and HMWHA by Capillary Electrophoresis

Procedure:

1. Experimental Parameters:

Analytes: low molecular weight hyaluronic acid (LMWHA, 350 KDa; Freda); high molecular weight hyaluronic acid (HMWHA, 2000 KDa; Freda)

Instrument: Beckman P/ACE MDQ system

Detector: Photodiode array (UV 200 nm)

Capillary: uncoated fused silica (50/60 cm; ID: 50 µm)

Sample injection: 10 psi, 20 s

Separation: 20 KV

Temperature: 25° C.

Buffer: 25 mM di-Sodium tetraborate anhydrous ($Na_2B_4O_7$) containing 25 mM Dodecyl sulfate sodium salt ($NaCl_{12}H_2.5SO_4$) and 10% Polyethylene glycol (PEG 8000).

2. Prepared stock sample solution: Samples of LMWHA (20 mg) and HMWHA (20 mg) were put together into a 100 ml, volumetric flask and dissolved with an aqueous solution of pH 6.8 phosphate buffer, and than stirred (990 rpm) for 2 h to get 200 ppm concentration solution.

3. 5 mL of stock sample solution was transferred to a 10 mL volumetric flask, and the solution was diluted to 100 ppm concentration with pH 6.8 phosphate buffer to same volume of the flask. 10 ml solution was filtered through 0.45 filter.

4. 200 ul solution was taken to put into a vial and following with analysis by CE for 20 min during detection.

Result:

FIG. 2 shows that the mixture of LMWHA and HMWHA can be definitely differentiated by the capillary electrophoretic (CE) analysis at the time around 12 minutes since start. The result explains that average high and low molecular weight HAs were existed separately without interconnecting each other even mix of LMWHA and HMWHA.

Example 2

The Degradation of HA in 1 U/ml HAase

Procedure:

1. 0.25 g High molecule weight sodium hyaluronate powder (HMWHA; Mw: 2000 KDa; Freda) and 0.25 g low molecule weight sodium hyaluronate powder (LMWHA; Mw: 350 KDa; Freda) were added into 50 ml PBS buffer (Phosphate buffered saline) respectively to form 0.5% solution, and then stirred for 6 hours until the powder was totally dissolved.

2. 0.05 g LMWHA powder and 0.2 g HMWHA powder (ratio 2:8; medium molecular weight sodium hyaluronate powder, MMWHA) were added into 50 ml PBS buffer, and then stirred for 6 hours until the powder was totally dissolved.

3. Mobile phase solution of GPC (Gel permeation chromatography) system was prepared by: (1) adding 35.49 g $Na_2HPO_4$ powder into 450 ml deionized distilled water (dd water) and stirred for 30 minutes in room temperature to form 0.5 M $Na_2HPO_4$ solution; and (2) adding 18 g $NaH_2PO_4$ powder into 250 ml dd water and stirred for 30 minutes in room temperature to form 0.5 M $NaH_2PO_4$ solution.

4. 1 U/ml HAase was prepared by dissolving HAase powder into PBS buffer in 4° C.

5. 2 ml HA sample, 1 ml 10 U/ml HAase and 7 ml PBS buffer were mixed for 3 minutes by vortex in 15 ml glass tube.

6. The tube was shaken by 50 rpm in water bath. 1 ml solution was taken after the 15, 30, 45, 60, 75, 90, 105, 120 minutes and then supplied with 1 ml HAase each time. Every 1 ml solution was filtered through 0.45 µm filter. 20 µl solution was injected into GPC system and then the diagram was recorded.

7. The situation of GPC system were (1) column: 2×GMPW×1 (TSK-gel); (2) mobile phase flow rate: 1 ml/min; (3) temperature: 30☐.

8. All values in the table were expressed as means of n observations. The histological index was analyzed by Student's t-test.

Result:

FIG. 3 shows the retention time of GPC diagram. The vertical axis represents the retention time of GPC, the horizontal axis represents the incubation time of HA in solution containing HAase. The horizontal dotted lines from up to down represent the retention time of 2000 KDa, 1000 KDa, 350 KDa and 17 KDa HAs, respectively. Increase in retention time indicates degradation of HAs over time. After 15 min of incubation, the average Mw of HMWHA and MMWHA were decreased to about 1000 KDa. After 37 min of incubation, the average Mw of HMWHA and MMWHA were decreased to about 350 KDa. After 90 min of incubation, the average Mw of HMWHA, MMWHA and LMWHA were decreased to no obvious difference which were all larger than 17 KDa.

Example 3

The Degradation of HA in 0.1 N HCl

Procedure:

1. LMWHA, MMWHA and HMWHA were prepared as the same as Example 1

2. Mobile phase solution of GPC system was prepared as the same as Example 1

3. Artificial gastric juice (0.1 N HCl) was prepared by mixing 5.72 ml 17.5 N HCl and 90 ml dd water and stirred for 10 minutes as a stocking solution.

4. 2 ml of HMWHA, MMWHA and LMWHA were mixed with 8 ml artificial gastric juice, respectively in a 15 ml glass tube and by vortex for 3 minutes.

5. The tube was shaken by 50 rpm in 37° C. water bath. 1 ml solution was taken after the 6, 12, 24, 48 hours and then supplied with 1 ml artificial gastric juice each time. Every 1 ml solution was filtered through 0.45 μm filter. 20 μl solution was injected into GPC system and then the diagram was recorded.

6. All values in the table were expressed as means of n observations. The histological index was analyzed by Student's t-test.

Result:

FIG. 4 shows the retention time of GPC diagram. The vertical axis represents the retention time of GPC, the horizontal axis represents the incubation time of HA in artificial gastric juice. The horizontal dotted lines from up to down represent the retention time of 2000 KDa, 1000 KDa, 350 KDa and 17 KDa HAs, respectively. The retention time was slowly increased following prolonged incubation. After 7 hours of incubation, the average Mw of HMWHA and MMWHA were decreased to about 1000 KDa. After 31 hours of incubation, the average Mw of MMWHA was decreased to about 350 KDa. After 35 hours of incubation, the average Mw of HMWHA was decreased to about 350 KDa. The results indicated that HA was slowly decreased in the artificial gastric juice.

Example 4

The Adhesion of HA in Colon Tissue (IVIS Image System-Vision 3)

Procedure:

1. LMWHA and HMWHA were prepared as the same as Example 1. MMWHA (MMWHA; Mw: 1000 KDa; Freda) were added into 50 ml PBS buffer, and then stirred for 6 hours until the powder was totally dissolved and ready for use in the following steps.

2. Fluorescent HA (HA-0 was prepared by (1) 0.39 g MES free acid (2-(N-morpholino) ethanesulfonic acid, Calbiochem) and was dissolved in 100 ml dd water. (2) Solution A: 65 mg fluororesceinamine powder, (isomer I, Fluka) was dissolved in 9 ml 95% EtOH solution and then stirred for 10 minutes under a condition that light was prohibited. (3) Solution B: 359 mg EDC powder (N-(3-Dimethylamino propyl)-N-ethyl carbodiimide hydrochloride, Sigma) was dissolved in 9 ml MES buffer and then stirred for 10 minutes. (4) Solution C: 216 mg NHS powder (N-Hydroxysuccinimde, Sigma) was dissolved in 9 ml MES buffer and then stirred for 10 minutes. (5) 3 ml Solution A was slowly dropped into 50 ml 0.5% HA solution and then stirred for 10 minutes under a condition that light was prohibited. (6) 3 ml Solution B and 5 ml Solution C were separately dropped into the solution of step (5) and then stirred for 10 minutes under a condition that light was prohibited. (7) 0.02 M MES buffer was slowly added into the solution of step (6) until the volume reached 100 ml and then stirred for 24 hours at room temperature under a condition that light was prohibited. (8) The product after reaction was poured into a dialysis tubing (Mw: 12000~14000) in 5 L dd water as a dialysis solution and then stirred for 5 days at 4□ under a condition that light was prohibited with dialysis solution being changed every 12 hours until the dialysis solution had no fluorescence. (9) The liquid after dialysis was allocated into 50 c.c. plastic centrifuge tubes and then reserved at −20° C. refrigerator overnight followed by drying in a freeze-drying machine under a condition that light was prohibited. (10) The dried HA-f powder was reserved at −20° C. refrigerator. (11) 50 mg HA-f powder was slowly added into 10 ml PBS buffer and then stirred for 6 hours until the powder was totally dissolved.

3. Colon tissue of SD-rat (Sprague-Dawley Rat) aged 7-8 weeks was cut by scalpel and then washed by PBS buffer followed by being cut to 3-4 cm long with soaking in PBS buffer finally.

4. Injured colon tissue was prepared by brushing by toothbrush for 20 times longitudinally and then soaking in PBS buffer.

5. Normal and injured colon tissues were put into a 12-well plate and then 1 ml 0.5% HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times.

6. Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.

7. All values in the table are expressed as means of n observations. The histological index was analyzed by Student's t-test.

Result:

FIG. 5 shows the affinity of fluorescence-labelled HAs to colonic tissue as expressed by fluorescent index. The fluorescent index of normal colon tissue was defined as 1. The other colon tissues tests were calibrated by the defined value. The results showed HA in the same average Mw adhered more to physically scratched colonic tissue than to normal colonic tissue. The lower the Mw of HA, the higher they adhere to the normal or the physically scratched colonic tissue.

Example 5

Treatment Effects of PU98 on Rats that Had Aspirin Induced Gastrointestinal Ulcers Procedure:

1. Test substance

PU98 (composition of binary molecular weight of HA that are 70% HA with an average Mw of 2000 KDa and 30% HA with an average Mw of 1000 KDa in PBS solution, the final concentration is 0.5%; i.e. 0.5 g HA in 100 c.c. PBS solution).

2. Test Method (1) Test Animal

Thirty eight-weeks-old SPF Sprague-Dawley male rats (BioLASCO Taiwan Co., Ltd.), were divided into 3 groups: study group (Aspirin/PU98), placebo group (Aspirin/PBS), control group (PBS), each group consisting of 10 rats with 2 rats housed per cage at the Animal Technology Institute Taiwan rodents room.

(2) Animal Testing

Before animal experimentation, rats were first fasted for 24 hours or more. From day one (D1) of experimentation to day three (D3), rats were given 1 ml of Aspirin (200 mg/ml) through intraperitoneal administration.

From day 4 to day 18, rats of the study group were given 1 ml of Aspirin (100 mg/ml) daily through intraperitoneal administration, they were also fed a 2 ml dosage of PU98 once every morning and afternoon.

From day 4 to day 18, rats of the placebo group were given 1 ml of Aspirin (100 mg/ml) daily through intraperitoneal administration, however they were fed a 2 ml dosage of PBS (placebo) once every morning and afternoon.

From day 4 to day 18, rats of the control group were not given any Aspirin, but were fed a 2 ml dosage of PBS once every morning and afternoon.

Seven days after organization of groups, half of each group was randomly selected for dissection and studied for changes in gastrointestinal inflammation Fourteen days after organization of groups, all rats were dissected and studied for changes in gastrointestinal inflammation All rats and rat food were weighed daily; records were taken for weight and changes in food intake.

(3) Statistical Analysis

The present invention was analyzed by "student t test" to evaluate relationship between the study group, placebo group and control group.

Result:

The present invention used changes of average body weight as an convenient index to view the amelioration of PU. Thirty rats were used in the present invention to investigate the anti-inflammatory effect on stomach and duodenum of rat. From day 1 to day 3, rats were given 200 mg of Aspirin after having been fasted. On day 4, 11 of the total rats have died, and upon dissection internal abdominal bleeding was observed. Three separate groups were organized from the remaining rats with each group consisting of 6 rats. The study group was given 100 mg of Aspirin daily through intraperitoneal administration, as well as being fed with 2 ml dosage of PU98 every morning and afternoon. The placebo group was given 100 mg of Aspirin daily through intraperitoneal administration; however, they were fed with 2 ml dosage of PBS (placebo) every morning and afternoon. The control group was not administered any Aspirin but were fed with 2 ml dosage of PBS every morning and afternoon. During the medication period, after groups were organized, 1 rat died from both the study group and placebo group.

Seven days after organization of groups (D12), 3 rats from each group were dissected to observe changes in inflammation of the stomach and duodenum. Fourteen days after organization of groups (D19), all remaining rats were dissected to observe changes in inflammation of the stomach and duodenum. Gastric bleeding spots were observable in the study group as well as the placebo group.

Loss of weight was apparent when comparing rat weights between groups after being administered 200 mg of Aspirin. Rats of the placebo group and control group showed significant weight differences on D9-D19 (FIG. 6). Also, during the whole experiment, the result showed a trend that the study group kept heavier in body weight than the placebo group.

What is claimed is:

1. A method for treating and preventing peptic ulcers and duodenal ulcers, comprising a step of administering to a subject in need thereof a therapeutically effective amount of a hyaluronic acid mixture consisting essentially of a low average molecular weight hyaluronic acid (LMWHA) and a high average molecule weight hyaluronic acid (HMWHA), wherein the average molecular weight (Mw) of LMWHA 0.5 million Da, and the average Mw of HMWHA within 1.5 million to 3.5 million Da, and a mixing ratio of the LMWHA and the HMWHA is in a range from 20:80 to 80:20 by weight.

2. The method according to claim 1, wherein the mixing ratio of the LMWHA and HMWHA is 1:1.

3. The method according to claim 1, wherein the hyaluronic acid mixture is in a concentration range of 0.5 mg/ml to 10 mg/ml solved in phosphate buffered saline (PBS) or pharmaceutical buffer solution.

4. The method according to claim 1, wherein the hyaluronic acid mixture includes an excipient to formulate an oral solid dosage form, oral or injection solution; and wherein administration routes includes oral or endoscope injection.

5. The method according to claim 1, wherein the hyaluronic acid mixture conjunctively used with a coagulant, antacid, H2 blocker, potassium hydrogen ion pump blocker or mucosa protector as an adjuvant to potentiate the drug effect.

6. The method according to claim 1, wherein the hyaluronic acid mixture is also treating and preventing bleeding caused by peptic ulcer or duodenal ulcer.

* * * * *